US00PP27244P3

(12) United States Plant Patent
Shoup

(10) Patent No.: US PP27,244 P3
(45) Date of Patent: Oct. 11, 2016

(54) ***ROSA* HYBRID PLANT NAMED 'BBARE'**

(50) Latin Name: ***Rosa* hybrid**
Varietal Denomination: BBARE

(71) Applicant: George Michael Shoup, Brenham, TX (US)

(72) Inventor: George Michael Shoup, Brenham, TX (US)

( * ) Notice: Subject to any disclaimer, the term of this patent is extended or adjusted under 35 U.S.C. 154(b) by 112 days.

(21) Appl. No.: 14/544,446

(22) Filed: Jan. 7, 2015

(65) Prior Publication Data

US 2016/0198602 P1 Jul. 7, 2016

(51) Int. Cl.
*A01H 5/02* (2006.01)

(52) U.S. Cl.
USPC ..... Plt./103

(58) Field of Classification Search
USPC ..... Plt./103
CPC ..... A01H 5/0222
See application file for complete search history.

*Primary Examiner* — Kent L Bell
(74) *Attorney, Agent, or Firm* — Samuel R. McCoy, Jr.

(57) ABSTRACT

'BBARE' is a distinctive variety of *Rosa* hybrid which is characterized by the combination of a shrubby growth habit, a medium plant size, canes with few thorns, a recurrent bloom habit with moderate to strong bloom fragrance, a double-petal flower with a high petal count, a near-white flower color at anthesis, as well as the stability and uniformity of traits through successive cycles of asexual propagation.

2 Drawing Sheets

Latin name of the genus and species: The Latin name of the genus and species of the novel variety disclosed herein is *Rosa* hybrid.

Variety denomination: The inventive variety of *Rosa* hybrid disclosed herein has been given the variety denomination 'BBARE'.

BACKGROUND OF THE INVENTION

The present invention relates to a new and distinct *Rosa* hybrid, shrub rose cultivar, which has been given the variety denomination of 'BBARE'.

Parentage: The new *Rosa* hybrid cultivar 'BBARE' originated as a naturally occurring, partial-plant mutation of *Rosa* hybrid 'Belinda's Dream' (unpatented). Said mutation was initially discovered by the inventor in March of 2014 in a cultivated field of the parent plant at the inventor's commercial nursery in Brenham, Tex. The inventor observed one cane of an individual 'Belinda's Dream' plant which was producing near-white flowers instead of the characteristic medium pink flowers of 'Belinda's Dream'. At that time, three stem cuttings were taken from the cane that was producing the white flowers. The resulting plants were isolated for further observation and to confirm uniformity and stability of the distinguishing characteristic. Subsequent cuttings were taken from these three plants which yielded a consistent crop of white-blooming plants. The new cultivar was given the name 'BBARE' in November of 2014.

Asexual Reproduction: 'BBARE' was first asexually propagated by vegetative cuttings in March of 2014 at a commercial nursery in Brenham, Tex. under the control of the inventor and has since been vegetatively propagated through one additional generation. The distinctive characteristics of the inventive 'BBARE' variety are stable from generation to generation; plants of the variety produced by asexual reproduction maintain the distinguishing characteristics of the original plant.

SUMMARY OF THE INVENTION

The following characteristics have been repeatedly observed and represent the distinguishing characteristics of the new *Rosa* hybrid cultivar 'BBARE'. These traits in combination distinguish 'BBARE' as a new and distinct cultivar.

1 *Rosa* hybrid 'BBARE' exhibits a shrubby growth habit; and
2. *Rosa* hybrid 'BBARE' exhibits a medium plant size; and
3. *Rosa* hybrid 'BBARE' exhibits canes with few thorns; and
4. *Rosa* hybrid 'BBARE' exhibits a recurrent bloom habit with moderate to strong flower fragrance; and
5. *Rosa* hybrid 'BBARE' exhibits a double-type flower; and
6. *Rosa* hybrid 'BBARE' exhibits a near-white perianth color, at anthesis.

BOTANICAL DESCRIPTION OF THE PLANT

Figure 1:
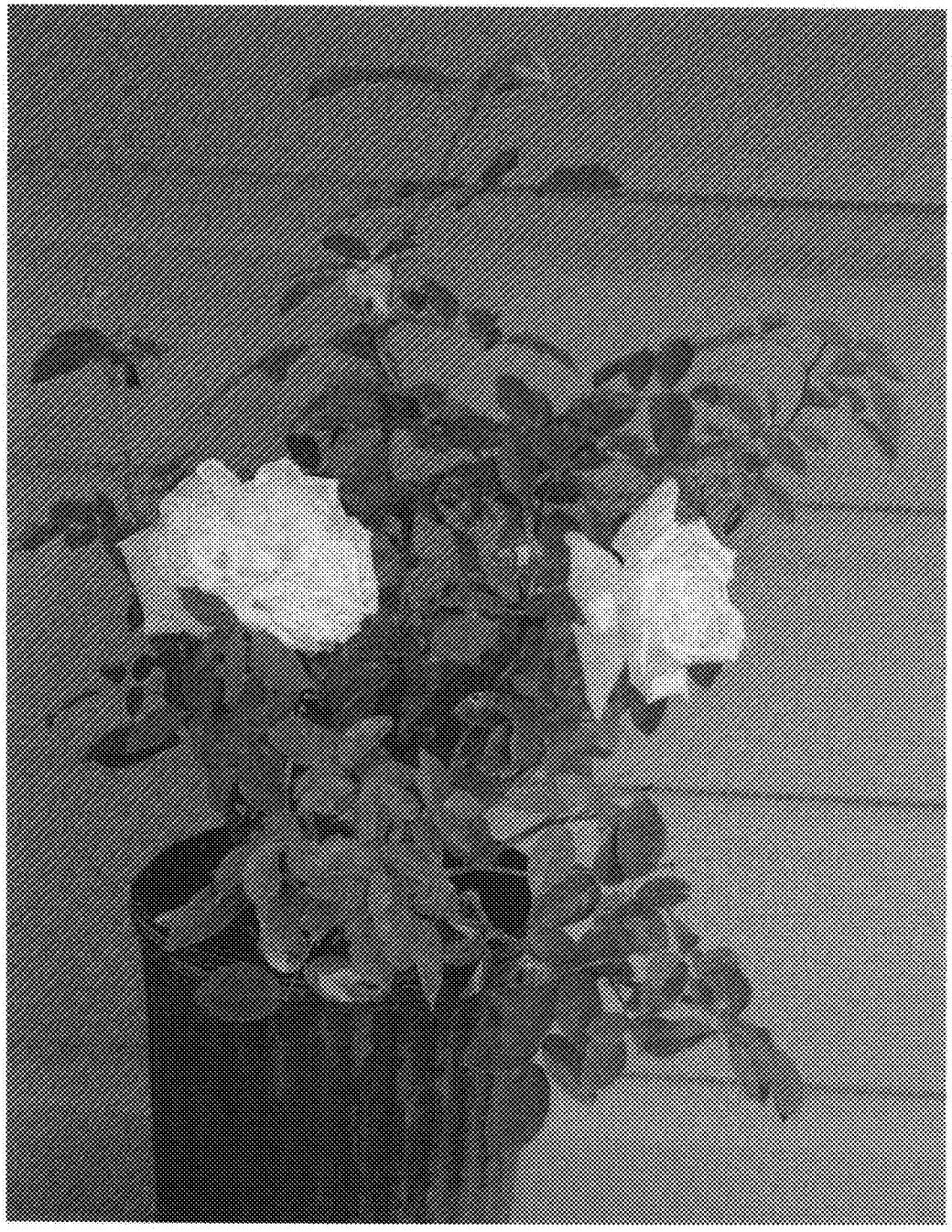
FIG. 1 shows, as nearly true as it is reasonably possible to make the same in color illustrations of this type, an exemplary specimens of the new cultivar, 'BBARE'. The plant shown is approximately 2 years old and were grown outdoors, in full sun, at a commercial nursery in Brenham, Tex. Said plant was maintained with slow-release granular fertilizer and regular overhead irrigation. No artificial light, photoperiodic treatments or chemical treatments were given to the plants.
Figure 2:
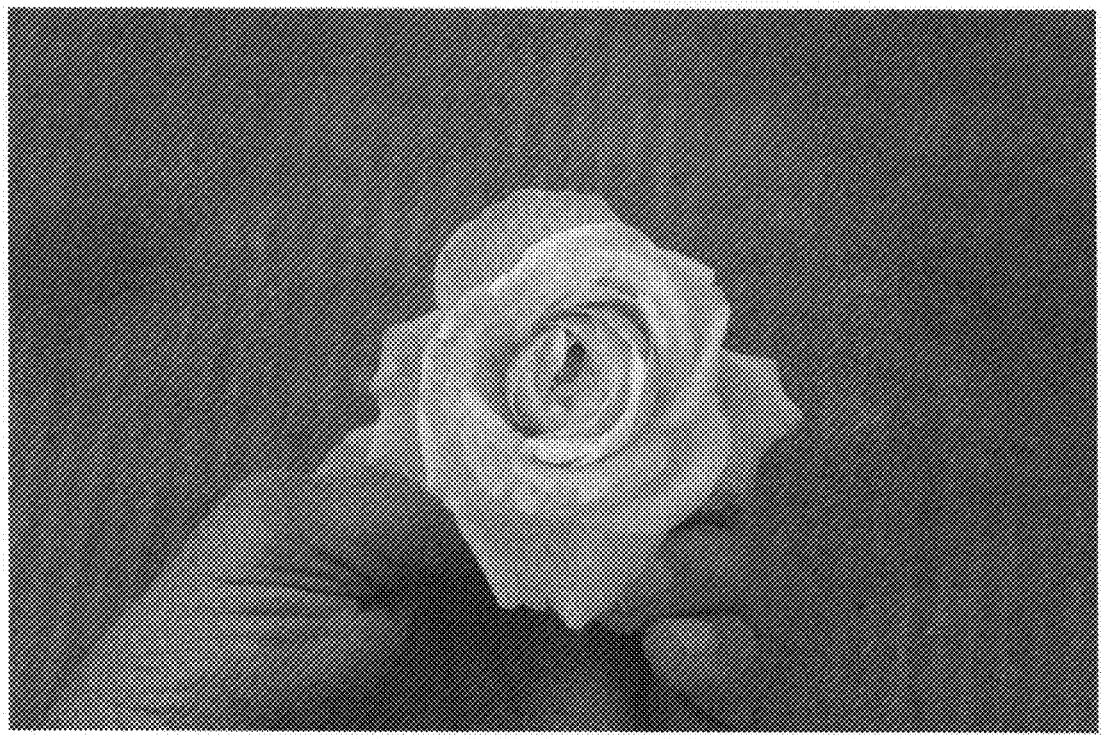
FIG. 2 shows, as nearly true as it is reasonably possible to make the same in color illustrations of this type, the flower of 'BBARE'.

The following is a detailed botanical description of a new and distinct variety of *Rosa* hybrid known as 'BBARE', based upon observations of a plant, approximately 2 years old, grown outdoors, in full sun, at a commercial nursery in Brenham, Tex. Said plant was maintained with slow-release granular fertilizer and regularly watered with overhead irrigation. No artificial light, photoperiodic treatments, or chemical treatments were given to the plants. Observation data was recorded in November of 2014.

Those skilled in the art will appreciate that certain characteristics will vary with older or, conversely, with younger plants. 'BBARE' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart,* The Royal Horticultural Society, London, 1986 edition.

A botanical description of 'BBARE' and comparisons with other varieties of *Rosa* hybrid are provided below.

Technical Description of the Variety

Plant description:

*Growth rate.*—Moderately vigorous; approximately 50 cm per growing season.

*Growth habit.*—Upright, shrubby.

*Mature dimensions.*—168 cm tall and 107 cm wide, on average.

*Cold hardiness.*—USDA Hardiness Zones 5 to 10.

*Propagation.*—Vegetative cuttings using semi-soft wood.

*Time to initiate roots.*—Approximately 7 to 14 days to initiate roots at 20° Centigrade.

*Time to produce a rooted cutting.*—Approximately 21 days to produce a rooted cutting at 20° Centigrade.

*Disease and pest resistance.*—Neither tolerance nor resistance to normal diseases and pests of *Rosa* hybrid have been observed.

*Drought resistance.*—Requires regular irrigation, in common with the parent.

Root system: Fibrous.

Stem:

*Immature stems.*—Dimensions — Length is variable with age, the longest observed is 330 mm long; greatest observed diameter is approximately 7 mm. Cross-section — Round. Color — A combination of yellow-green (near RHS 144A) and greyed-purple (RHS 183D) but generally appearing as greyed-purple 183D. Texture — Glabrous; matte. Internodal Spacing — Ranging from 25 to 30 mm.

*Mature stems.*—Dimensions — Approximately 435 mm long and 10 mm wide. Cross-section — Round. Color — Green (RHS 143C). Texture — Glabrous; matte.

*Thorns.*—Thorn Density — Generally, from 0 to 3 thorns per node, on mature stems. Thorn Shape — Concave; downward facing. Thorn Dimensions — Approximately 10 mm long and 6 mm wide at the base. Thorn Color — Greyed-purple 184B.

Foliage:

*Leaves.*—Leaf structure — Odd-pinnately compound leaves; immature terminal leaves consisting of 3 pinna, immature axillary leaves consisting of 5 pinna, and mature axillary leaves consisting of 7 pinna. Pinna are borne on petiolules; terminal petiolule measuring approximately 14 to 16 mm long and 2.0 to 2.5 mm wide and axillary petiolule measuring approximately 6 mm long and 1.5 mm wide. In mature leaves, rachis measures approximately 40 mm long and 2.0 to 2.5 mm wide. Color of rachis and petiolules both appear as greyed-purple (RHS 187A), adaxially, and a combination of greyed-purple (RHS 187A) and greyed-orange (RHS 164B), abaxially. Leaf arrangement — Alternate. Petioles — Approximately 18 mm long and 2 to 3 mm wide; color is greyed-purple (RHS 187A), adaxially, and a combination of greyed-purple (RHS 187A) and greyed-orange (RHS 164B), abaxially. Stipules — Attachment is adnate; shape is scale-like; approximately 14 mm long and 6 mm wide; margins are serrulate.

*Pinna.*—Shape — Broad ovate. Apex — Acute. Base — Rounded. Dimensions — Average of 46 mm in length and 24 mm in width. Texture (adaxial & abaxial surfaces) — Glabrous; matte. Margin — Serrate. Immature Color (adaxial surface) — Green (RHS 137C), flushed with greyed-purple 183B. Immature Color (abaxial surface) — Glaucous; Yellow-green (RHS 147C), flushed with greyed-purple 183B. Mature Color (adaxial surface) — Green (RHS 137A). Mature Color (abaxial surface) — Glaucous; yellow-green (RHS 147C. Venation — Reticulate. Vein color (adaxial surface) — In immature foliage, greyed-purple (RHS 187A); in mature foliage, yellow-green (RHS 146D). Vein color (abaxial surface) — In immature foliage, greyed-purple (RHS 187A); in mature foliage, midrib is yellow-green (RHS 146D) and all other veins are green (RHS 137B).

Inflorescence and flower:

*Inflorescence.*—Terminal buds; typical solitary but may occur in clusters of two or three.

*Bloom habit.*—Recurrent throughout spring, summer, and fall.

*Rate of flower opening.*—Approximately 7 days from bud to fully opened flower.

*Flower longevity on plant.*—Approximately 10 days.

*Fragrance.*—Moderately perfumed with a fruity, raspberry-like, fragrance.

*Peduncle.*—Dimensions — Approximately 60 mm long and 4 mm wide. Strength — Medium. Texture — Smooth. Color — A combination of yellow-green (near RHS 144A) and greyed-purple (RHS 183D) but generally appearing as greyed-purple 183D.

*Bud, prior to bud break.*—Shape — Ovate. Dimensions — Approximately 25 mm long and 15 mm wide. Bud Color — Yellow-green (near RHS 144A).

*Perianth.*—Individual Flowers; Corolla — Arrangement is a whorl with loosely-held outer petal and tightly whorled inner petals. The diameter of the corolla ranges from 63 mm to 100 mm, with an average diameter of 76 mm; the approximate depth of corolla ranges from 50 mm to 65 mm, at the deepest point (i.e. the center of the corolla). Petal Description — Quantity — Approximately 45 to 50. Dimensions — Approximately 44 mm long and 40 mm wide. Margin — Slightly undulate; reflexed at and near the apex. Shape — Obovate. Apex — Rounded to cordate. Base — Broadly cuneate. Texture — Glabrous; matte; velvety. Color, Fully Opened Flower — Mature, Outer Petals — Both the upper and lower surfaces are White (near RHS 155D); base of the petal appearing as Yellow (RHS 12C). Immature, Inner Petals — Both the upper and lower surfaces are white (near RHS 155D) at and near the apex, transitioning to Red (RHS 36C) at the petal's interior, transitioning to Yellow (RHS 14D) at and near the base; entire petal fading to White (RHS 155D) with age.

*Sepals.*—Sepal Texture — Dull; exterior is lightly puberulent and interior is heavily pubescent. Sepal Arrangement — Rotate; reflexed. Quantity — Five Shape — Lanceolate. Margin — Entire. Apex — Cuspidate. Base — Broad cuneate. Dimensions — Average 30 mm long and 6 mm wide. Color (interior surface) — Yellow-green (RHS 144A). Color (exterior surface) — Yellow-green (RHS 145B).

Reproductive organs:

*Stamens.*—Number — Numerous; approximately 40 to 50. Filament Length — Approximately 6 to 7 mm. Filament Color — Yellow (RHS 15D). Anther Length — Approximately 2 mm. Anther Color — Yellow (RHS 15A). Anther Shape — Irregular ovate to near oblong. Pollen Quantity — Moderate to high. Pollen Color — Yellow (RHS 15A).

*Pistil.*—Number — Numerous; approximately 30. Pistil Length, Including Style and Stigma — Approximately 7 to 8 mm. Stigma Shape — Irregular, flattened. Stigma Color — Yellow-white (RHS 159A). Style Length — Approximately 2 mm. Style Color — Yellow (RHS 15A). Ovary Position — Inferior.

*Hypanthium.*—Shape — Pitcher shaped. Dimensions — 8 mm in length and 8 mm wide. Color — Yellow-green (near RHS 144A).

Seed and fruit: Not observed.

Comparisons with the Parent

Plants of the new cultivar 'BBARE' are comparable to the parent variety *Rosa* hybrid 'Belinda's Dream' (unpatented) in all characteristics with the exception of the flower color. 'BBARE' exhibits near-white flowers at anthesis whereas the parent exhibits medium-pink flowers at anthesis.

That which is claimed is:

1. A new and distinct variety of *Rosa* hybrid plant named 'BBARE', substantially as described and illustrated herein.

* * * * *